United States Patent
Ziegler

(10) Patent No.: US 6,861,435 B2
(45) Date of Patent: Mar. 1, 2005

(54) UROKINASE INHIBITORS

(75) Inventor: Hugo Ziegler, Witterswil (CH)

(73) Assignee: Pentapharm AG (CH)

( * ) Notice: Subject to any disclaimer, the term of this patent is extended or adjusted under 35 U.S.C. 154(b) by 0 days.

(21) Appl. No.: 10/472,367

(22) PCT Filed: Mar. 19, 2002

(86) PCT No.: PCT/CH02/00162

§ 371 (c)(1),
(2), (4) Date: Sep. 18, 2003

(87) PCT Pub. No.: WO02/074756

PCT Pub. Date: Sep. 26, 2002

(65) Prior Publication Data

US 2004/0110831 A1 Jun. 10, 2004

(30) Foreign Application Priority Data

Mar. 21, 2001 (CH) ................................ PCT/CH01/00178

(51) Int. Cl.[7] .................. A61K 31/495; C07D 207/06; C07D 207/10; C07D 295/04
(52) U.S. Cl. .................. 514/255.01; 514/423; 544/390; 548/537; 562/126
(58) Field of Search ........................... 514/255.01, 423; 544/390; 548/537; 562/126

(56) References Cited

FOREIGN PATENT DOCUMENTS

| WO | WO 96/05189 | 2/1996 |
|---|---|---|
| WO | WO 00/04954 | 2/2000 |
| WO | WO 00/17158 | 3/2000 |

OTHER PUBLICATIONS

Kim et al.; Rational Design of Selective Thrombin Inhibitors; Bioorganic & Medicinal Chemistry Letters; vol. 7, No. 7; pp 769–774, 1997.
Oh et al.; Discovery of LB30057, A Benzamidrazone–Based Selective Oral Thrombin Inhibitor; Bioorganic & Medicinal Chemistry Letters 8; (1998) pp. 639–634.
Zega et al., Design and Structure–Activity Relationship of Thrombin Inhibitors with an Azaphenylalanine Scaffold; Potency and Selectivity Enhancements Via P2 Optimization; Bioorganic & Medicinal Chemistry 9; (2001), pp. 2745–2756.
Oh et al.; Discovery of LB30057, A Benzamidrazone–Based Selective Oral Thrombin Inhibitor; Bioorganic & Medicinal Chemistry Letters 8; (1998) pp. 631–634.
Sturzebecher et al.; 3–Amidinophenylalanine–based Inhibitors of Urokinase; Bioorganic & Medicinal Chemistry Letters 9; (1999), pp. 3147–3152.
Sturzebecher et al; Synthesis and Structure–Activity Relationships of Potent Thrombin Inhibitors: Piperazides of 3–Amidinophenylalanine; J. Med. Chem; 1997, 40, pp. 3091–3099.
Zega et al; Novel Thrombin Inhibitors with Azaphenylalanine Scaffold; Pharmazie; vol. 56, pp. 683–685; (2001).

*Primary Examiner*—Taofiq Solola
(74) *Attorney, Agent, or Firm*—Hoffmann & Baron, LLP

(57) ABSTRACT

The invention relates to the compounds of general formula (I), that are present with respect to $R^1$ as racemates as well as L- or D-configured compounds and as E/Z mixtures as well as E or Z isomers and in which the various symbols are defined as in the description and the claims, as well as to the salts thereof, for use as therapeutic agents and for diagnostic purposes. The inventive compounds can be processed to medicaments or to diagnostic agents that are used for the diagnosis, therapy and prevention of urokinase- or urokinase-receptor associated diseases, for example for the treatment of tumors. The compounds are highly efficient in inhibiting growth and/or spread of malign tumors, for example tumor spread of pancreatic cancer, tumor growth of breast cancer and the formation of tumor metastases. The compounds of formula (I) and the salts thereof can be produced by conventional methods.

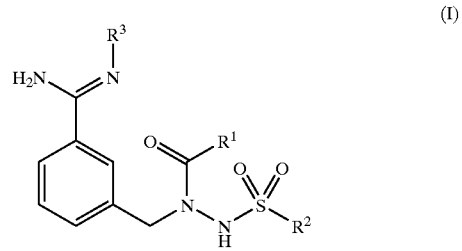

27 Claims, No Drawings

UROKINASE INHIBITORS

Proteolytic processes play an important part in the propagation and metastasizing of solid tumors. For assembling and disassembling the structures in their immediate environment, they have not only procoagulant substances at their disposal, but also enzymes of the fibrinolytic system. Although the (patho)biochemical connections are not yet definitely elucidated, a central significance is obviously to be attributed to the plasminogen activator urokinase and to the urokinase receptor. Therefore, the development of urokinase inhibitors can be highly useful first of all to further elucidate the role of urokinase and urokinase receptor in different diseases, particularly in tumor propagation and metastasizing. Moreover, urokinase inhibitors represent potential drugs for influencing tumor invasion.

Urokinase is a proteolytic enzyme and belongs to the group of trypsin-like enzymes which, in proteins and peptides, cleave the bonds of the basic amino acids arginine and lysine. Therefore, most inhibitors known until now have a strongly basic group, e.g., an amidino function. The first urokinase inhibitors efficient in the micromolar region were found among bis-benzamidines and naphthamidine-derived compounds (J. Stürzebecher and F. Markwardt, Pharmazie 33, 599–602, 1978). Compounds which also inhibit urokinase with micromolar $K_i$ values and have a guanidino function such as amilorides (J.-D. Vassalli and D. Belin, FEBS Lett. 214, 187–191, 1987) and phenylguanidines (H. Yang et al., J. Med. Chem. 33, 2956–2961, 1990) were described later. Benzothiophene-2-carboxamidines were described as highly effective inhibitors ($K_i$ at 0.2 μmol/l) (M. J. Towle et al., Cancer Res. 53, 2553–2559, 1993).

Nα-arylsulfonylated and Nα-arylsulfonyl-aminoacylated derivatives of 3-amidinophenylalanine are known to be selective inhibitors of thrombin (F. Markwardt et al., Thromb. Res. 17, 425–431, 1980), of the clotting factor Xa (J. Stürzebecher et al., Thromb. Res. 54, 245–252, 1989), and of urokinase (P. Wikstroem et al., WO 00/17158 and J. Stürzebecher et al., WO 00/04954), respectively. In the variation of the phenylalanine group, we have found that replacing the CH function of phenylalanine by a nitrogen atom while simultaneously introducing a (hetero) aryl residue at the sulfonyl moiety increases the affinity towards urokinase very decisively. Therefore, α-(3-amidinobenzyl)-β-(hetero)arylsulfonyl hydrazides and the prodrugs obtained by replacing the amidino function with an amidoxim residue (see D. Baucke et al., WO 00/61577) represent new groups of urokinase inhibitors.

The present invention relates to new urokinase inhibitors of the general formula I,

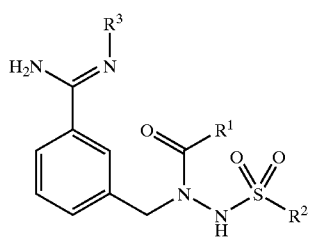

(I)

which referring to $R^1$ are present as racemates as well as L- or D-configured compounds, respectively, and as E/Z-mixtures as well as E- or Z-isomers, respectively, and wherein $R^1$ represents
(a) OH or ($C_1$–$C_8$)-alkoxy optionally substituted with aryl or ($C_3$–$C_8$)-cycloalkyloxy; or
(b) a group of formula —N($R^4R^5$), wherein $R^4$ and $R^5$—independently of each other—represent hydrogen, ($C_1$–$C_8$)-alkyl, ($C_1$–$C_8$)-alkyl optionally substituted with 1 to 3-times identically or differently substituted aryl, ($C_3$–$C_8$)-cycloalkyl, ($C_3$–$C_8$)-cycloalkyl-($C_1$–$C_4$)-alkyl, $NH_2$, $NHR^6$ or $NR^6R^7$, wherein $R^6$ and $R^7$—independently of each other—represent ($C_1$–$C_8$)-alkyl, ($C_3$–$C_8$)-cycloalkyl, optionally 1 to 3-times identically or differently substituted aryl, optionally 1 to 3-times identically or differently substituted heteroaryl, or $R^6$ and $R^7$ together with the nitrogen atom to which they are bound represent a thiazoline, thiazolidine, oxazoline, oxazolidine or morpholine ring, which can be substituted 1 to 3-times identically or differently; or
(c) a group of formula

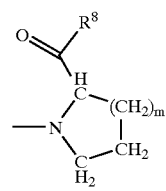

(A)

wherein m represents integer 1 or 2 and wherein one of the methylene groups can be substituted with a hydroxyl, carboxyl or ($C_1$–$C_8$)-alkyl residue or a substituted ($C_1$–$C_8$)-alkyl residue with an optionally 1 to 3-times identically or differently substituted aryl, and $R^8$ has one of the above denotations of $R^1$ mentioned under (a) and (b), wherein a further aromatic or cycloaliphatic ring can be condensed in position 2,3 or 3,4 related to the nitrogen atom; or
(d) a group of formula

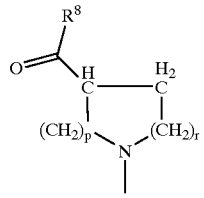

(B)

wherein p and r—independently of each other—can be 1 or 2 and wherein one of the methylene groups can be substituted with a hydroxyl, carboxyl, ($C_1$–$C_8$)-alkyl- or a ($C_1$–$C_8$)-alkyl residue substituted with an optionally 1 to 3-times identically or differently substituted aryl, and $R^8$ has one of the above denotations of $R^1$ mentioned under (a) and (b), wherein a further aromatic or cycloaliphatic ring can be condensed in position 2,3 or 3,4 related to the nitrogen atom; or
(e) a piperidyl group which is optionally substituted with a ($C_1$–$C_8$)-alkylcarbonyl, a ($C_1$–$C_8$)-alkoxycarbonyl, a ($C_1$–$C_4$)-alkyl or a hydroxyl residue in one of the positions 2, 3 and 4, wherein a further aromatic or cycloaliphatic ring can be condensed in position 2,3 or 3,4 related to the nitrogen atom; or (f) a group of formula

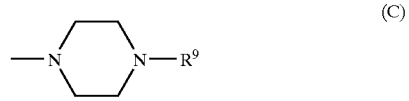

(C)

wherein $R^9$ represents H, $(C_1-C_8)$-alkyl, $(C_2-C_8)$-alkenyl, $(C_2-C_8)$-alkinyl, formyl, $(C_1-C_8)$-alkylcarbonyl, $(C_2-C_8)$-alkenylcarbonyl, $(C_2-C_8)$-alkinyl-carbonyl, cyano, $(C_1-C_8)$-alkoxycarbonyl, $(C_2-C_8)$-alkenyloxycarbonyl, $(C_2-C_8)$-alkinyloxycarbonyl, $(C_3-C_8)$-cycloalkyl, $(C_3-C_8)$-cycloalkylcarbonyl, $(C_3-C_8)$-cycloalkyloxycarbonyl, $(C_3-C_8)$-heterocyclyl, $(C_3-C_8)$-heterocyclyl-carbonyl, $(C_3-C_8)$-heterocyclyloxycarbonyl with 1 to 3 heteroatoms each; aryl, arylcarbonyl, aryloxycarbonyl; heteroaryl, heteroarylcarbonyl, heteroaryloxycarbonyl with 1 to 3 heteroatoms each; a carboxamide residue of formula —CON($R^4R^5$) or a thiocarboxamide residue of formula —CSN($R^4R^5$), wherein $R^4$ and $R^5$—independently of each other—represent hydrogen, $(C_1-C_8)$-alkyl, $(C_2-C_8)$-alkenyl, $(C_2-C_8)$-alkinyl, $(C_3-C_8)$-cycloalkyl, aryl or heteroaryl, or $R^4$ and $R^5$ together with the nitrogen atom to which they are bound form a 5- to 7-member ring which can comprise 1 to 2 further heteroatoms (N, O, S) and which can be 1 to 3-times identically or differently substituted, or a —SO$_2$Y residue, wherein Y represents $(C_1-C_8)$-alkyl, $(C_2-C_8)$-alkenyl, $(C_2-C_8)$-alkinyl, $(C_3-C_8)$-cycloalkyl, aryl, heteroaryl, aryloxy or N($R^4R^5$); wherein all the alkyl, alkenyl and alkinyl residues of the alkyl-, alkenyl- and alkinyl-, respectively, containing groups can be substituted 1 to 3-times identically or differently and all the cycloalkyl, heterocyclyl, aryl and heteroaryl residues of the cycloalkyl-, heterocyclyl-, aryl- and heteroaryl-, respectively, containing groups can be substituted 1 to 3-times identically or differently;

$R^2$ represents an aryl or heteroaryl residue optionally substituted 1 to 3-times identically or differently or a camphor residue; and $R^3$ represents hydrogen, amino or hydroxy; wherein these compounds can be present as free bases as well as salts with inorganic acids or as salts with organic acids.

In general, the compounds of formula I are present as salts with inorganic acids, preferably as hydrochlorides, or as salts with organic acids.

The compounds of formula I and their salts can be manufactured according to the present invention as follows:

(a) for the manufacture of a compound of formula I, wherein $R^3$ represents hydrogen or amino, conversion of a cyano compound of formula

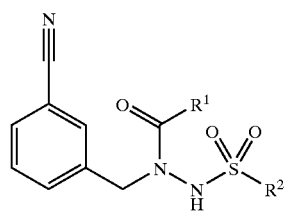

10 wherein $R^1$ and $R^2$ have the denotation mentioned above, by addition of H$_2$S to the cyano group, into the corresponding thioamide from which a thioimidoester is obtained by S-alkylation. This thioimidoester is finally transformed into the amidino or amidrazone compound, respectively, by treatment with ammonia or hydrazine or a salt thereof; or (b) for the manufacture of a compound of formula I, wherein $R^3$ represents hydrogen or amino, conversion of a cyano compound of formula 10 by acidic alcoholysis into an acid addition salt of the corresponding imidoester whose transformation with ammonia or hydrazine leads to the amidino or amidrazone compound, respectively; or (c) for the manufacture of a compound of formula I, wherein $R^3$ represents hydrogen, reduction of a compound of formula I, wherein $R^3$ means OH, or a corresponding alkanoyloxy compound; or (d) for the manufacture of a compound of formula I, wherein $R^3$ represents OH or NH$_2$, conversion of a cyano compound of formula 10 into the corresponding hydroxyamidine or amidrazone compound, respectively, using hydroxylamine or hydrazine; and (e) if desired, conversion of an obtained compound of formula I into an acid addition salt and/or conversion of an obtained acid addition salt into the corresponding compound of formula I or into another salt of an added acid.

The initial products of above defined formula 10 are also objects of the present invention.

The term "alkyl", taken for itself alone or as a structure element for alkyl-containing groups, refers to saturated hydrocarbon residues which can be straight or branched. The term "cyclolakyl", also taken for itself alone or as a structure element for cycloalkyl-containing groups, refers to cyclic, saturated hydrocarbon residues. The terms "alkenyl" and "alkinyl", again taken for themselves alone or as structure elements for alkenyl or alkinyl-containing groups, respectively, refer to straight or branched hydrocarbon residues with at least one C—C double or triple bond, respectively. The terms "alkoxy" and "cycloalkyloxy" refer to alkyl or cycloalkyl groups bound with an oxygen group in the sense of above definitions of "alkyl" or "cycloalkyl", respectively.

Examples for alkyl—as a group and as a structure element for alkyl-containing groups—are methyl, ethyl, propyl, n-butyl, n-pentyl, n-hexyl and n-octyl as unbranched residues and isopropyl, tert. butyl, isobutyl, sec. butyl and isoamyl as branched residues. Preferred are methyl and ethyl. Examples for cycloalkyl—as a group and as a structure element for cycloalkyl-containing groups—are cyclopropyl, cyclobutyl, cyclopentyl and cyclohexyl. Examples for alkenyl—as a group and as a structure element for alkenyl-containing groups—are a.o. vinyl, 1-methylvinyl, allyl, 1-butenyl and 2-hexenyl as unbranched residues and isopropenyl as branched residue. Examples for alkinyl—as a group and as a structure element for alkinyl-containing groups—are propargyl, 2-butinyl or 5-hexinyl as unbranched residues and 2-ethinylpropyl or 2-propargylisopropyl as branched residues.

The term "aryl" refers to mono, di or multinuclear aromatic hydrocarbon residues, e.g. phenyl or naphthyl, preferably phenyl.

The term "heteroaryl", for itself alone or as a structure element for heteroaryl-containing groups, refers to 5 to 11-member aromatic systems composed of one or two rings, wherein 1 to 3 members are heteroatoms, selected among oxygen, sulphur and nitrogen. 1 to 2 benzene rings can be condensed to the heterocycle. Examples thereof are pyridyl, pyrimidinyl, pyridazinyl, pyrazinyl, 1,3,5-triazinyl, quinolinyl, isoquinolinyl, quinoxalinyl, quinazolinyl, phthalazinyl, pyrrolyl, pyrazolinyl, imidazolinyl, 1,2,4- triazolinyl, tetrazolinyl, furyl, thienyl, oxazolinyl, thiazolinyl, isothiazolinyl, benzoxazolyl, benzothienyl, indolyl, benzimidazolyl, indazolyl, benzotriazolyl and benzothiazolyl. The connection can occur either at the hetero moiety or at the benzo moiety and in the π-excess heteroaromates at the nitrogen or any carbon.

The term "heterocyclyl"—for itself alone and as a structure element for heterocyclyl-containing groups—refers to a 3 to 8-member, 1 to 3 heteroatom (selected among O, S and N)-containing non-aromatic ring, to which a benzene ring can be condensed. Examples thereof are oxiranyl, pyrrolidinyl, piperidinyl, piperazinyl, morpholinyl, azepinyl, oxazolidinyl, oxazolinyl, thiazolidinyl, thiazolinyl and 1,2,3,4-tetrahydroquinolinyl.

Substituents of the optionally substituted aryl- and heteroaryl groups are e.g. halogen, $C_1-C_6$-alkyl, $C_1-C_6$-haloalkyl, hydroxy, $C_1-C_6$-alkoxy, $C_1-C_6$-haloalkoxy, $C_1-C_6$-alkenyl, $C_2-C_6$-alkenyloxy, $C_2-C_6$-alkinyl, $C_3-C_6$-alkinyloxy, $C_1-C_6$-alkoxycarbonyl, CN, OCN, nitro, amino, $C_1-C_6$-alkylamino, di-$C_1-C_6$-alkylamino, aminocarbonyl, $C_1-C_6$-alkylaminocarbonyl, di-$C_1-C_6$-alkylaminocarbonyl, $C_1-C_6$-alkylthio, $C_1-C_6$-alkylsulfoxyl, $C_1-C_6$-alkylsulfonyl, $C_3-C_6$-cycloalkyl, optionally substituted benzyl, optionally substituted phenyl, optionally substituted phenoxy or optionally substituted phenylcarbonyl. The above mentioned aromatic rings can be substituted with 1 to 3 identical or different substituents, selected from the group composed of halogen, cyano, nitro, $C_1-C_6$-alkyl, $C_1-C_6$-haloalkyl, $C_1-C_6$-alkoxy, $C_1-C_6$-haloalkoxy, hydroxy, amino, $C_1-C_6$-alkylamino, di-$C_1-C_6$-alkylamino and $C_1-C_6$-alkoxycarbonyl.

Substituents of the optionally substituted, 5 to 7-member rings formed by $NR^4R^5$ and $NR^6R^7$ and of the heterocyclyl groups are e.g. halogen, $C_1-C_6$-alkyl, $C_1-C_6$-haloalkyl, hydroxy, $C_1-C_6$-alkoxy, CN, OCN, nitro, amino, $C_1-C_6$-alkylamino, di-$C_1-C_6$-alkylamino, $C_1-C_6$-alkylthio, $C_1-C_6$-alkylsulfoxyl, $C_1-C_6$-alkylsulfonyl, $C_3-C_6$-cycloalkyl, optionally substituted benzyl, optionally substituted phenyl or optionally substituted phenoxy. The above mentioned aromatic rings can be substituted with 1 to 3 identical or different substituents, selected from the group composed of halogen, cyano, nitro, $C_1-C_6$-alkyl, $C_1-C_6$-haloalkyl, $C_1-C_6$-alkoxy, $C_1-C_6$-haloalkoxy, hydroxy, amino, $C_1-C_6$-alkylamino, di-$C_1-C_6$-alkylamino and $C_1-C_6$-alkoxycarbonyl.

Substituents of the optionally substituted alkyl, alkenyl and alkinyl residues and of the groups containing these residues are e.g. halogen, hydroxy, $C_1-C_6$-alkoxy, halo-$C_1-C_6$-alkoxy, $C_1-C_6$-alkoxycarbonyl, optionally substituted phenyl and cyano.

The further ring optionally condensed at the heterocyclic residue of formula (A) or (B) or at the piperidine residue is preferably a benzene or cyclohexane ring.

Halogen is fluorine, chlorine, bromine and iodine, preferably fluorine and chlorine. Haloalkyl and haloalkoxy residues which are substituted with more than one halogen atom can bear identical or different halogen atoms.

Among the compounds of formula I, those wherein $R^1$ means OH, $(_1-C_8)$-alkoxy optionally substituted with aryl, $(C_3-C_8)$-cycloalkyloxy or a group of formula —$NR^4R^5$, (B) or (C), are preferred. Particularly preferred are those compounds of formula I, wherein $R^1$ represents a group of formula (C), wherein $R^9$ means formyl, $(C_1-C_8)$-alkylcarbonyl, $(C_2-C_8)$-alkenylcarbonyl, $(C_2-C_8)$-alkinylcarbonyl, $(C_1-C_8)$-alkoxycarbonyl, $(C_2-C_8)$-alkenyloxycarbonyl, $(C_2-C_8)$-alkinyloxycarbonyl or a carboxamide residue of formula —$CON(R^4R^5)$, wherein $R^4$ and $R^5$ represent hydrogen, $(C_1-C_8)$-alkyl, $(C_2-C_8)$-alkenyl or $(C_2-C_8)$-alkinyl, in particular those wherein $R^9$ means methoxycarbonyl, ethoxycarbonyl, benzyloxycarbonyl, dimethylaminocarbonyl or acetyl.

$R^2$ represents e.g. phenyl, 4-tolyl, 2,4,6-trimethylphenyl, 2,4,6-triisopropylphenyl, 4-methoxy-2,3,6-trimethylphenyl, 2,2-dimethyl-6-methoxychromanyl, 2,2,5,7,8-pentamethylchromanyl, anthraquinonyl, 1-naphthyl, 2-naphthyl, 5-(dimethylamino)-naphthyl, quinolyl, isoquinolyl, or a camphor residue, preferably 2,4,6-triisopropylphenyl.

$R^3$ preferably means hydrogen.

The preparation of the compounds of formula I and the primary products of formula 10 needed that for is further explained in the following figure 1.

Fig. 1: Preparation of the compounds of formula (I)

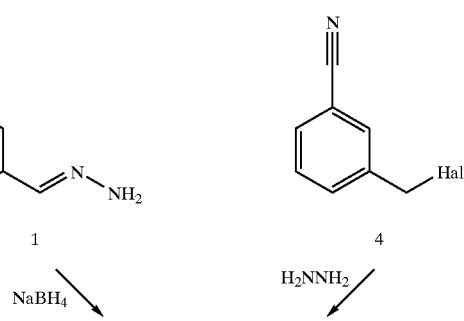

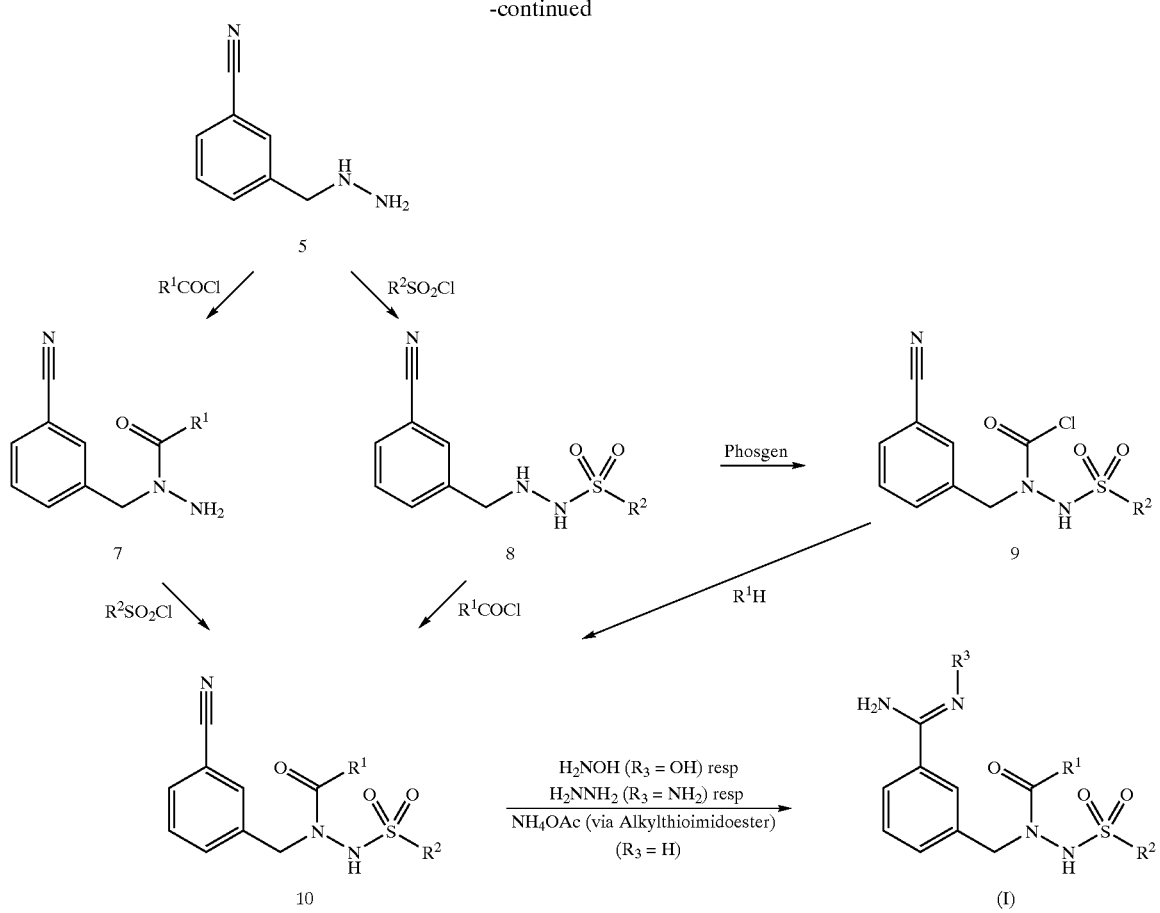

The compounds of general formula I with an amidine structure ($R^3$=H) can be obtained from the cyano compounds 10 in a known way. In general, addition of $H_2S$ to the cyano group first gives the corresponding thioamides which are converted into the corresponding thioimidoesters by S-alkylation, e.g. S-methylation with methyl iodide, and finally into the corresponding amidino compounds by treatment with ammonia or a salt thereof, e.g. ammonium acetate in alcoholic solution (see e.g. WO 94/18185, p. 23f; WO 00/17158, p. 5ff). Moreover, the corresponding imidoester salts, e.g. imidoester hydrochlorides, the conversion of which using ammonia, e.g. in alcoholic solution, leads to the corresponding amidino compounds, can also be manufactured from the cyano compounds of formula 10 by acidic alcoholysis, e.g. with methanol or ethanol in the presence of HCl gas and in certain cases of an inert solvent. Furthermore, these amidino compounds can be obtained by reduction, e.g. by palladium-catalyzed hydrogenation, of the corresponding hydroxyamidine compounds (formula I, $R^3$=OH) or of their acylated derivatives, e.g. the corresponding acetyloxyamidine compounds.

The compounds of general formula I with hydroxyamidine structure ($R^3$=OH) can be obtained from the cyano compounds of formula 10 using hydroxylamine, e.g. by conversion with an alcoholic hydroxylamine solution (see e.g. WO 00/61577, p. 36).

The compounds of general formula I with amidrazone structure ($R^3$=$NH_2$) can be obtained from the cyano compounds via the thioimidoesters or imidoesters, as mentioned above, or directly by reaction with an alcoholic hydrazine solution (see e.g. Pavlov, P. A.; Kul'nevich, V. G.; Khim. Geterotsikl. Soedin. (1986), (2), 181–186).

A cyano compound of formula 10 can be prepared by
(aa) reacting a hydrazide of formula 7 with a sulfochloride of general formula $R^2SO_2Cl$ or a sulfonic acid anhydride of general formula $(R^2SO_2)_2O$, wherein $R^2$ has the previously mentioned denotation; or
(bb) converting a sulfonyl hydrazide of formula 8 with an acid chloride of general formula $R^1COCl$ or an anhydride of general formula $(R^1CO)_2O$, wherein $R^1$ has the previously mentioned denotations; or
(cc) converting a sulfonyl chlorocarbonyl hydrazide of formula 9 with a nucleophile of general formula $R^1H$, wherein $R^1$ has the previously mentioned denotation.

The above reaction types (aa) to (cc) are known and the cyano compound 10 can be prepared analogously.

A sulfonyl chlorocarbonyl hydrazide of formula 9 can be prepared by reacting a sulfonyl hydrazide of formula 8 with phosgen, diphosgen or triphosgen, e.g. similarly to the method described in J. Org. Chem. 41, 3763 (1976).

The compounds of general formulas 7 and 8 can be synthesized as shown in Fig. 1 according to known ways and methods.

The urokinase inhibitors of the present invention are adequate for use as therapeutic agents or for diagnostic purposes. They can be processed either to drugs, containing a compound of formula I or a salt thereof and possibly at least one additive appropriate to a drug, or to diagnostic products, containing a compound of formula I or a salt thereof and possibly at least one additive appropriate to a diagnostic product, respectively. The compounds of formula I or their salts or products containing same, respectively, can be used for the diagnosis, therapy and prevention of urokinase or urokinase receptor-associated diseases, for example for the treatment of tumors, because they are highly efficient in inhibiting growth and/or propagation of malignant tumors, e.g. tumor propagation in pancreatic cancer, tumor growth in breast cancer as well as tumor metastasizing. They are particularly appropriate against breast carcinoma, pancreas carcinoma and metastasis formation, as well as against *pemphigus vulgaris*.

The mentioned products can contain one or several compounds of formula I or salts thereof in combination with at least one further pharmacologically active substance, e.g. with at least one radio-labelling and/or at least one cytotoxic substance.

Drugs containing a compound of formula I or a salt thereof can be administered orally, topically, rectally or parenterally, e.g. subcutaneously or intravenously. These drugs are available in the form of tablets, dragées, capsules, pellets, suppositories, solutions, plasters or other transdermal systems.

The compounds and salts of the present invention can be applied together with other antitumor substances or with other types of treatment, e.g. radiotherapy or surgical operations.

It is worthy to note that the compounds and salts of the present invention influence blood coagulation only slightly as they have too high $K_i$ values for an effective inhibition of thrombin and factor Xa.

The following examples further illustrate the invention without limiting its scope in any way.

EXAMPLES OF PREPARATION

Fig. 2:

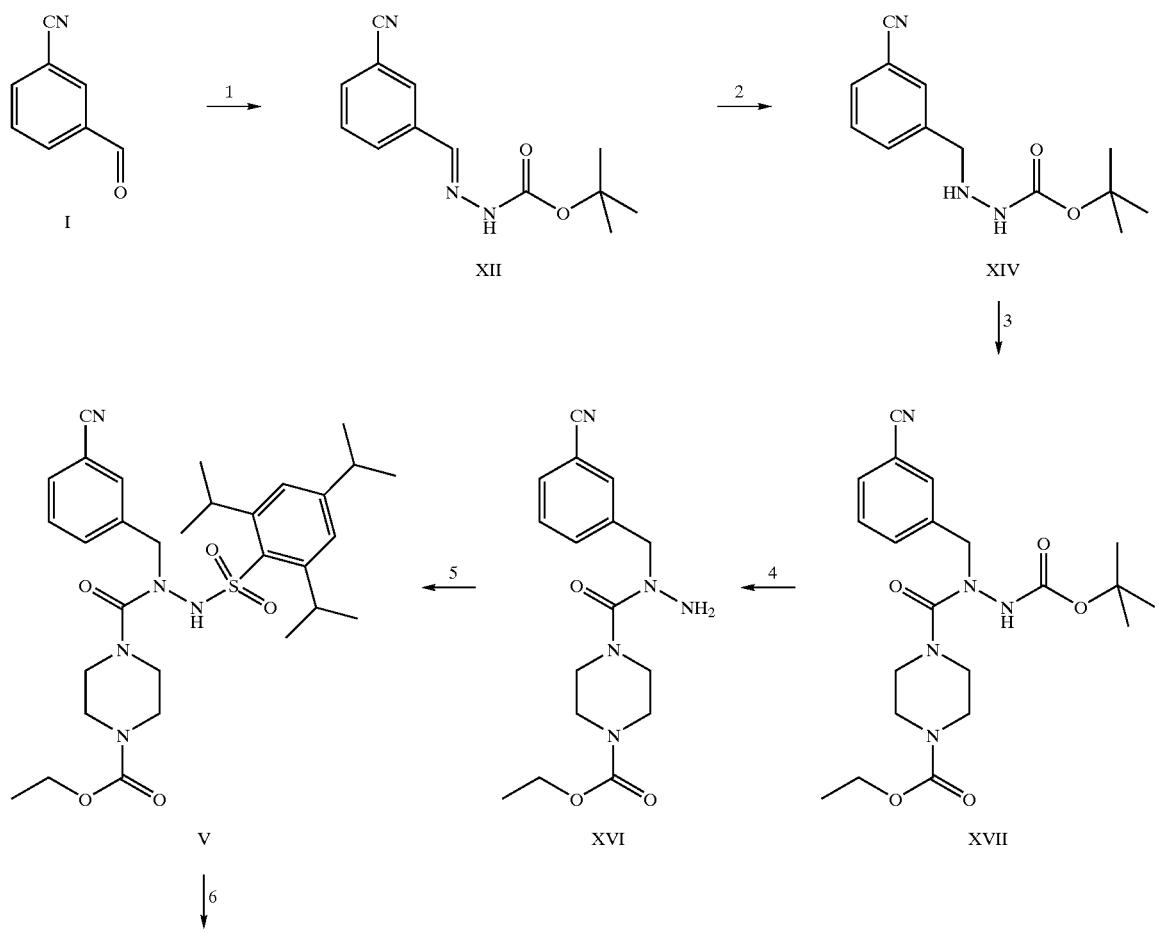

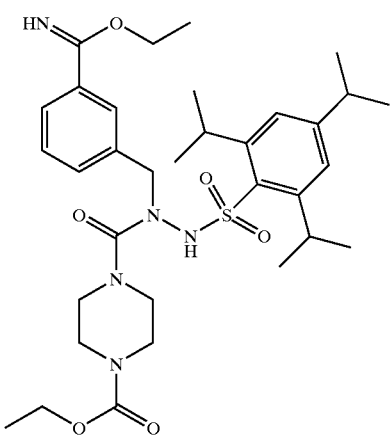

XXI

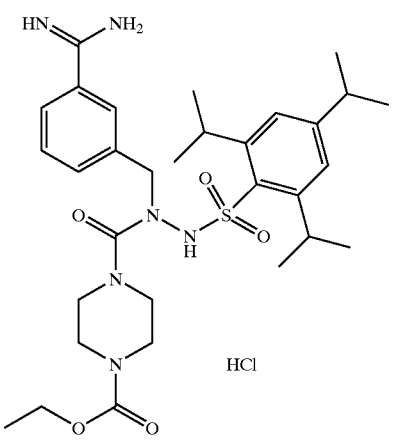

VII

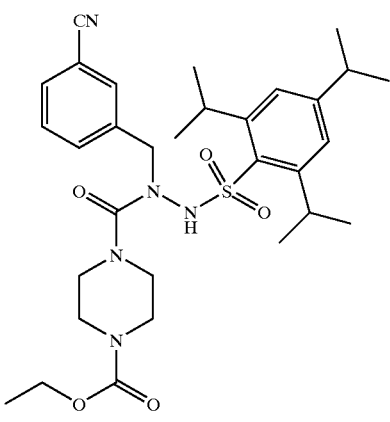

V

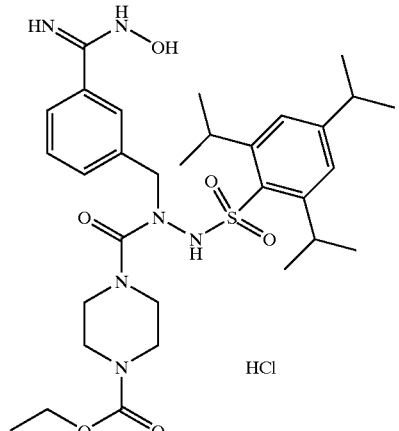

VI

The compounds according to Fig. 2 were prepared as follows:

3-Cyanobenzaldehyde-(1,1-dimethyl)-ethoxycarbonyl-hydrazone XII: 1 mmol of 3-cyanobenzaldehyde and 1 mmol of t-butylcarbazate were refluxed in 2.5 ml of acetic ether. The obtained suspension was cooled to 0° C. and the solid was filtered. The mother liquor was concentrated and the obtained crystals were filtered again. Yield: 74%.

$^1$H-NMR (500 MHz, DMSO): 1.48 (s, 9H), 7.62 (t, 1H), 7.83 (dt, 1H), 7.95 (dt, 1H), 8.01 (t, 1H), 8.04 (s, 1H), 8.5 (broad, 1H).

$^{13}$C-NMR: 28.5 (3C), 80.1, 112.3, 118.8, 130.34 (2), 130.36, 130.8, 132.9, 136.3, 152.6.

1-(3-Cyanobenzyl)-2-[(1,1-dimethyl)-ethoxycarbonyl]-hydrazine XIV: 1 g of XII was hydrogenated in 10 ml of ethanol with 0.1 mol % of Pd/C at room temperature. The reaction mixture was filtered over a suction filter with Celite and the obtained cake was washed with ethanol. The filtrate was concentrated and the residue was dried. Yield: 98%.

$^1$H-NMR (500 MHz, DMSO): 1.39 (s, 9H), 3.95 (s, 2H), 5.10 (s, 1H), 7.51 (t, 1H), 7.64 (dt, 1H), 7.71 (dt, 1H), 7.80 (s, 1H), 8.5 (broad, 1H).

$^{13}$C-NMR: 28.5 (3C), 46.0, 78.7, 111.4, 119.4, 129.5 (2C), 130.8 (2C), 144.6, 152.6.

1-Ethoxycarbonyl-4-[1-(3-cyanobenzyl)-2-((1,1-dimethyl)-ethoxycarbonyl)-1-hydrazino-carbonyl]-piperazine XVII: a solution of 2 mmol of XIV and 3 mmol of diisopropylethylamine (DIPEA) in 4 ml of CH$_2$Cl$_2$ was added dropwise to a solution of 1 mmol of triphosgen in 2 ml of CH$_2$Cl$_2$ at room temperature. After 15 minutes a solution of 2 mmol of piperazine-1-ethyl carboxylate and 3 mmol of DIPEA in 4 ml of CH$_2$Cl$_2$ was added dropwise. The mixture was stirred for 1 hour, washed with 10% citric acid and saturated NaHCO$_3$ solution, dried over Na$_2$SO$_4$ and finally concentrated. The residue was purified by chromatography (silica gel, acetic ether/hexane 2:3).

$^1$H-NMR (500 MHz, DMSO): 1.15 (t, 3H), 1.32 (s, 9H), 3.2–3.4 (m, br, 9H), 4.05 (q, 2H), 4.3–4.4 (br, 2H), 7.53 (t, 1H), 7.64 (d, 1H), 7.73 (d, 1H), 7.75 (s, 1H).

$^{13}$C-NMR: 14.9, 28.3 (3C), 40.7, 45.6 (2C), 53.7 (2C), 61.2, 89.0, 111.2, 119.2, 130.0, 131.5, 132.2, 133.6, 155.0, 157.6, 165.5.

MS (ESI): 432.5 [M$^+$+H], 376, 332, 185, 159.

Yield: 50%

1-Ethoxycarbonyl-4-[1-(3-cyanobenzyl)-1-hydrazino]-carbonyl-piperazine XVI: 1 g of XVII was dissolved in 10 ml of CH$_2$Cl$_2$ and added to 3 ml of trifluoroacetic acid at 0° C. The reaction mixture was stirred for 3.5 hours at room temperature and afterwards extracted with 10% citric acid. The aqueous phase was made basic by the addition of saturated Na$_2$CO$_3$ solution and extracted with CH$_2$Cl$_2$. The organic phase was concentrated and the residue was dried under high vacuum. Yield: 82%.

$^1$H-NMR (500 MHz, DMSO): 1.19 (t, 3H), 3.0–3.5 (m, br, 10H), 4.05 (q, 2H), 4.45 (s, 2H), 7.52 (t, 1H), 7.62 (d, 1H), 7.72 (s, 1H), 7.75 (d, 1H).

$^{13}$C-NMR: 14.9, 40.7, 45.9 (2C), 56.0 (2C), 61.2, 111.4, 119.3, 129.6, 131.2, 132.4, 133.9, 155.0, 163.5, 169.1, 176.6.

MS (ESI): 332.4 [M$^+$+H], 185, 159, 142, 101.

1-Ethoxycarbonyl-4-[1-(3-cyanobenzyl)-2-(2,4,6-triisopropylbenzenesulfonyl)-1-hydrazino-carbonyl]-piperazine V: 1 mmol of XVI was dissolved in 4 ml of CH$_2$Cl$_2$ and added to 1.5 mmol of triisopropylbenzenesulfonylchloride. The reaction mixture was refluxed, added to 3.5 mmol of DIPEA and stirred for 48 hours under reflux. The reaction mixture was washed with 10% citric acid and concentrated. The residue was purified by chromatography (silica gel, acetic ether/hexane 1:3).

$^1$H-NMR (500 MHz, DMSO): 1.2–1.4 (m, 21H), 2.9 (m, 1H), 3.0–3.5 (m, 10H), 3.9 (m, 2H), 4.1 (q, 2H), 4.5 (br, 1H), 7.22 (s, 2H), 7.40–7.48 (m, 2H), 7.53 (s, 1H), 7.71 (dt, 1H).

MS (ESI): 598.6 [M$^+$+H], 330, 251, 233, 185, 159.

Yield: 55%

1-Ethoxycarbonyl-4-[1-(3-(ethoxy-imino-methyl)-benzyl)-2-(2,4,6-triisopropyl-benzenesulfonyl)-1-hydrazino-carbonyl]-piperazine XXI: Gaseous hydrochloric acid was applied for 30 minutes in a cooled solution of 1 mmol of V in 30 ml of ethanol. The solution was stirred for 1 h at room temperature and finally evaporated. Yield: 100%.

MS (ESI): 644.6 [M$^+$+H], 481, 348, 163.

1-Ethoxycarbonyl-4-[1-(3-(amino-imino-methyl)-benzyl)-2-(2,4,6-triisopropyl-benzenesulfonyl)-1-hydrazino-carbonyl]-piperazine hydrochloride VII: 1 mmol of XXI was dissolved in 15 ml of ethanol, added to 3 mmol of NH$_4$OAc and stirred for 4 h at 60° C. The solvent was evaporated and the crude product was purified by preparative HPLC (H$_2$O, acetonitrile). Yield: 47%.

$^1$H-NMR (500 MHz, DMSO): 1.1–1.3 (m, 21H), 2.91 (qq, 1H), 3.0–3.4 (m, 10H), 3.99 (qq, 2H), 4.04 (q, 2H), 7.20 (s, 2H), 7.30 (d, 1H), 7.48 (t, 1H), 7.63 (s, 1H), 7.70 (d, 1H), 9.18 (s, 1H), 9.38 (s, 1H), 9.56 (s, 1H).

$^{13}$C-NMR: 28.5, 23.8 (4C), 25.5 (2C), 29.7, 33.8 (2C), 45.3, 56.4 (2C), 56.7 (2C), 61.2, 124.0 (2C), 126.0, 127.6, 128.0, 129.3, 133.0, 133.8, 137.3, 150.6 (2C), 155.4, 154.9, 160.8, 165.9.

MS (ESI): 615.6 [M$^+$+H, free base].

1-Ethoxycarbonyl-4-[1-(3-(amino-hydroxyimino-methyl)-benzyl)-2-(2,4,6-triiso-propylbenzenesulfonyl)-1-hydrazino-carbonyl]-piperazine hydrochloride VI: 1 mmol of V was dissolved in 30 ml of ethanol, added to 5 mmol of hydroxylamine hydrochloride and 2 ml of 10% NaCO$_3$, and stirred for 2 hours under reflux. The solvent was evaporated. The residue was dissolved in 70 ml of EtOAc and washed with 60 ml of water and 50 ml of 1N HCl. The crude product was purified by preparative HPLC (H$_2$O, acetonitrile). Yield: 60%.

$^1$H-NMR (500 MHz, DMSO): 1.2–1.4 (m, 21H), 2.9 (m, 1H), 3.0–3.5 (m, 10H), 3.9–4.1 (m, 4H), 4.4 (br, 1H), 7.05 (m, 3H), 7.28–7.35 (m, 1H), 7.53 (m, 2H), 9.3 (s, 1H).

MS (ESI): 631.6 [M$^+$+H], 335, 150.

The compounds listed in Table 1 can be prepared according to the above mentioned methods.

TABLE 1

| No. | R$^1$ | R$^2$ | R$^3$ |
|---|---|---|---|
| 1. | 4-Formylpiperazinyl | 2,4,6-Triisopropylphenyl | H |
| 2. | 4-Acetylpiperazinyl | 2,4,6-Triisopropylphenyl | H |
| 3. | 4-Propionylpiperazinyl | 2,4,6-Triisopropylphenyl | H |
| 4. | 4-Methoxycarbonyl-piperazinyl | 2,4,6-Triisopropylphenyl | H |

TABLE 1-continued

| No. | R$^1$ | R$^2$ | R$^3$ |
|---|---|---|---|
| 5. | 4-Ethoxycarbonyl-piperazinyl | 2,4,6-Triisopropylphenyl | H |
| 6. | 4-Propoxycarbonyl-piperazinyl | 2,4,6-Triisopropylphenyl | H |
| 7. | 4-(n-Butoxy)-carbonyl-piperazinyl | 2,4,6-Triisopropylphenyl | H |
| 8. | 4-Allyloxycarbonyl-piperazinyl | 2,4,6-Triisopropylphenyl | H |
| 9. | 4-Propargyloxycarbonyl-piperazinyl | 2,4,6-Triisopropylphenyl | H |
| 10. | 4-Aminocarbonyl-piperazinyl | 2,4,6-Triisopropylphenyl | H |
| 11. | 4-Ethylaminocarbonyl-piperazinyl | 2,4,6-Triisopropylphenyl | H |
| 12. | 4-Dimethylaminocarbonyl-piperazinyl | 2,4,6-Triisopropylphenyl | H |
| 13. | 4-Diethylaminocarbonyl-piperazinyl | 2,4,6-Triisopropylphenyl | H |
| 14. | 4-Benzyloxycarbonyl-piperazinyl | 2,4,6-Triisopropylphenyl | H |
| 15. | 4-Ethoxycarbonyl-piperazinyl | 2,4,6-Trimethylphenyl | H |
| 16. | 4-Ethoxycarbonyl-piperazinyl | 2,4,6-Triisopropylphenyl | OH |
| 17. | 4-Acetylpiperazinyl | 2,4,6-Triisopropylphenyl | OH |
| 18. | 4-Ethoxycarbonyl-piperazinyl | 2,4,6-Triisopropylphenyl | NH$_2$ |
| 19. | 4-Acetylpiperazinyl | 2,4,6-Triisopropylphenyl | NH$_2$ |

Determination of the Urokinase-inhibiting Activity

To determine the inhibitory activity, 200 μl of Tris buffer (0.05 mol/l, containing the inhibitor, 0.154 mol/l of NaCl, 5% ethanol, pH 8.0), 25 μl of substrate (Pefachrome UK or Bz-βAla-Gly-Arg-pNA in H$_2$O; Pentapharm Ltd., Basel, Switzerland) and 50 μl of sc-urokinase (Ribosepharm GmbH, Haan, Germany) were incubated at 25° C. After 3 min the reaction was stopped by the addition of 25 μl of acetic acid (50%) and the absorption was determined at 405 nm by means of a microplate reader (MR 50001 Dynatech, Denkendorf, Germany). The $K_i$ values were determined according to Dixon by linear regression using a computer program. The $K_i$ values represent the mean from at least 3 determinations.

The $K_i$ values mentioned in Table 2 can be determined according to the above mentioned method.

TABLE 2

| Compound of example | $K_i$ in μmol/l |
|---|---|
| 5 | 0.67 ± 0.18 |
| 18 | 25.6 ± 9.5 |

What is claimed is:

1. Compounds of the general formula I

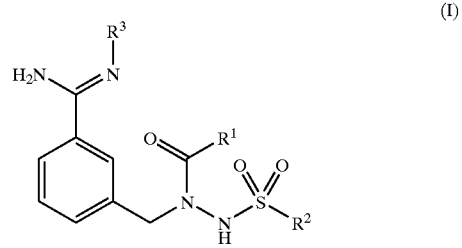

(I)

which referring to R$^1$ are present as racemates as well as L- or D-configured compounds, respectively, and as E/Z-mixtures as well as E- or Z-isomers, respectively and wherein $R^1$ represents (a) OH or $(C_1-C_8)$-alkoxy optionally substituted with aryl or $(C_3-C_8)$-cycloalkyloxy; or (b) a group of formula —$N(R^4R^5)$, wherein $R^4$ and $R^5$ independently of each other represent hydrogen, $(C_1-C_8)$-alkyl, $(C_1-C_8)$-alkyl optionally substituted with 1 to 3-times identically or differently substituted aryl, $(C_3-C_8)$-cycloalkyl, $(C_3-C_8)$-cycloalkyl-$(C_1-C_4)$-alkyl, $NH_2$, $NHR^6$ or $NR^6R^7$, wherein $R^6$ and $R^7$ independently of each other represent $(C_1-C_8)$-alkyl, $(C_3-C_8)$-cycloalkyl, optionally 1 to 3-times identically or differently substituted aryl, optionally 1 to 3-times identically or differently substituted heteroaryl, or $R^6$ and $R^7$ together with the nitrogen atom to which they are bound represent a thiazoline, thiazolidine, oxazoline, oxazolidine or morpholine ring, which can be substituted 1 to 3-times identically or differently; or (c) a group of formula

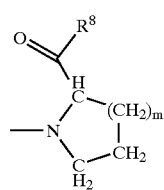

(A)

wherein m represents integer 1 or 2 and wherein one of the methylene groups can be substituted with a hydroxyl, carboxyl or $(C_1-C_8)$-alkyl residue or a $(C_1-C_8)$-alkyl residue substituted with an optionally 1 to 3-times identically or differently substituted aryl, and $R^8$ has one of the above denotations of $R^1$ mentioned under (a) and (b), wherein a further aromatic or cycloaliphatic ring can be condensed in position 2,3 or 3,4 related to the nitrogen atom; or (d) a group of formula

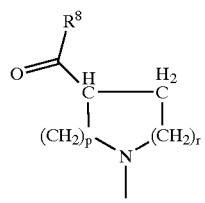

(B)

wherein p and r independently of each other can be 1 or 2 and wherein one of the methylene groups can be substituted with a hydroxyl, carboxyl, $(C_1-C_8)$-alkyl or a $(C_1-C_8)$-alkyl residue substituted with an optionally 1 to 3-times identically or differently substituted aryl, and $R^8$ has one of the above denotations of $R^1$ mentioned under (a) and (b), wherein a further aromatic or cycloaliphatic ring can be condensed in position 2,3 or 3,4 related to the nitrogen atom; or (e) a piperidyl group which is optionally substituted with a $(C_1-C_8)$-alkylcarbonyl, a $(C_1-C_8)$-alkoxycarbonyl, a $(C_1-C_4)$-alkyl or a hydroxyl residue in one of the positions 2, 3 and 4, wherein a further aromatic or cycloaliphatic ring can be condensed in position 2,3 or 3,4 related to the nitrogen atom; or (f) a group of formula

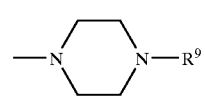

(C)

wherein $R^9$ represents H, $(C_1-C_8)$-alkyl, $(C_2-C_8)$-alkenyl, $(C_2-C_8)$-alkinyl, formyl, $(C_1-C_8)$-alkylcarbonyl, $(C_2-C_8)$-alkenylcarbonyl, $(C_2-C_8)$-alkinyl-carbonyl, cyano, $(C_1-C_8)$-alkoxycarbonyl, $(C_2-C_8)$-alkenyloxycarbonyl, $(C_2-C_8)$-alkinyloxycarbonyl, $(C_3-C_8)$-cycloalkyl, $(C_3-C_8)$-cycloalkylcarbonyl, $(C_3-C_8)$-cycloalkyloxycarbonyl; $(C_3-C_8)$-heterocyclyl, $(C_3-C_8)$-heterocyclyl-carbonyl, $(C_3-C_8)$-heterocyclyloxycarbonyl with 1 to 3 heteroatoms each; aryl, arylcarbonyl, aryloxycarbonyl; heteroaryl, heteroarylcarbonyl, heteroaryloxycarbonyl with 1 to 3 heteroatoms each; a carboxamide residue of formula —$CON(R^4R^5)$ or a thiocarboxamide residue of formula —$CSN(R^4R^5)$, wherein $R^4$ and $R^5$ independently of each other represent hydrogen, $(C_1-C_8)$-alkyl, $(C_2-C_8)$-alkenyl, $(C_2-C_8)$-alkinyl, $(C_3-C_8)$-cycloalkyl, aryl or heteroaryl, $R^4$ and $R^5$ together with the nitrogen atom to which they are bound form a 5- to 7-member ring which can comprise 1 to 2 further heteroatoms (N, O, S) and which can be optionally 1 to 3-times identically or differently substituted, or a —$SO_2Y$ residue, wherein Y represents $(C_1-C_8)$-alkyl, $(C_2-C_8)$-alkenyl, $(C_2-C_8)$-alkinyl, $(C_3-C_8)$-cyclo-alkyl, aryl, heteroaryl, aryloxy or $N(R^4R^5)$; wherein all the alkyl, alkenyl and alkinyl residues of the alkyl-, alkenyl- and alkinyl-, respectively, containing groups can be substituted 1 to 3-times identically or differently and all the cycloalkyl, heterocyclyl, aryl and heteroaryl residues of the cycloalkyl-, heterocyclyl-, aryl- and heteroaryl-, respectively, containing groups can be substituted 1 to 3-times identically or differently;

$R^2$ represents an aryl or heteroaryl residue optionally substituted 1 to 3-times identically or differently or a camphor residue; and $R^3$ represents hydrogen, amino or hydroxy;

wherein these compounds can be present as free bases as well as salts with inorganic acids or as salts with organic acids.

2. Compounds according to claim 1, wherein $R^1$ means OH, $(C_1-C_8)$-alkoxy optionally substituted with aryl, $(C_3-C_8)$-cycloalkyloxy or a group of formula —$NR^4R^5$, (B) or (C).

3. Compounds according to claim 2, wherein $R^1$ represent a group of formula (C), wherein $R^9$ means formyl, $(C_1-C_8)$-alkylcarbonyl, $(C_2-C_8)$-alkenylcarbonyl, $(C_2-C_8)$-alkinylcarbonyl, $(C_1-C_8)$-alkoxycarbonyl, $(C_2-C_8)$-alkenyloxycarbonyl, $(C_2-C_8)$-alkinyloxycarbonyl or a carboxamide residue of the formula —$CON(R^4R^5)$, wherein $R^4$ and $R^5$ represent each hydrogen, $(C_1-C_8)$-alkyl, $(C_2-C_8)$-alkenyl or $(C_2-C_8)$-alkinyl.

4. Compounds according to claim 3, wherein $R^9$ represents methoxycarbonyl, ethoxycarbonyl, benzyloxycarbonyl, dimethylaminocarbonyl or acetyl.

5. Compounds according to claim 1, wherein $R^2$ means phenyl, 4-tolyl, 2,4,6-trimethylphenyl, 2,4,6-triisopropylphenyl, 4-methoxy-2,3,6-trimethylphenyl, 2,2-dimethyl-6-methoxychromanyl, 2,2,5,7,8-pentamethylchromanyl, anthraquinonyl, 1-naphthyl, 2-naphthyl, 5-(dimethylamino)-naphthyl, quinolyl, isoquinolyl or a camphor residue.

6. Compounds according to claim 5, wherein $R^2$ means 2,4,6-triisopropylphenyl.

7. Compounds according to claim 1, wherein $R^3$ means hydrogen.

8. Compounds according to claim 1, wherein the compounds are present in the form of physiologically compatible acid salts.

9. Drugs comprising a compound according to claim 1 or a salt thereof and optionally at least one additive appropriate for a drug.

10. Diagnostic agent comprising a compound according to claim 1 or a salt thereof and optionally at least one additive approiate for a diagnostic agent.

11. A method for the treatment, diagnosis or prevention of a urokinase or urokinase receptor-associated disease comprising the step of administering to a mammal a pharmacological agent including at least one of the compounds according to claim 1.

12. The method of claim 11, wherein the agent is an antitumoral agent.

13. The method of claim 12, wherein the agent is an agent against one of the group consisting of breast cancer, pancreas cancer and metastasis formation.

14. The method of claim 11, wherein the agent is against *pemphigus vulgaris*.

15. Drugs according to claim 9, in combination with at least one other pharmacologically active substance.

16. Diagnostic agent according to claim 10, in combination with at least one other pharmacologically active substance.

17. The method according to claim 11, further comprising administering the agent in combination with at least one other pharmacologically active substance.

18. Drugs according to claim 15, wherein said other pharmacologically active substance is a radiolabelling and/or a cytotoxic substance.

19. Diagnostic agent according to claim 16, wherein said other pharmacologically active substance is a radiolabelling and/or cytotoxic substance.

20. The method according to claim 17, wherein said other pharmacologically active substance is a radiolabelling and/or cytotoxic substance.

21. Drugs according to claim 9, wherein said drugs are for oral, topical, rectal or parenteral administration, either alone or in combination with at least one other pharmacologically active substance.

22. Drugs according to claim 21, wherein said other pharmacologically active substance is a radiolabelling and/or cytotoxic substance.

23. The method according to claim 11, wherein said pharmacological agent is for oral, topical, rectal, or parentered administration, either alone or in combination with at least one other pharmacologically active substance.

24. The method according to claim 23, wherein said other pharmacologically active substance is a radiolabelling and/or toxic substance.

25. Drugs according to claim 21, wherein said drugs are in a form selected from the group consisting of tablets, dragées, capsules, pellets, suppositories, solutions, plasters, and other transdermal systems.

26. The method according to claim 23, wherein said administered pharmacological agent is in a form selected from the group consisting of tablets, dragées, capsules, pellets, suppositories, solutions, plasters, and other transdermal systems.

27. Method for the preparation of compounds of formula I defined in claim 1 and of acid addition salts thereof, which, (a) for the synthesis of a compound of formula I, wherein $R^3$ means hydrogen or amino, comprises the conversion of a cyano compound of formula

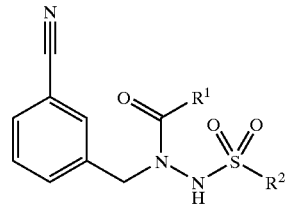

wherein $R^1$ and $R^2$ have the denotation given in claim 1, into the corresponding thioamide by the addition of $H_2S$ to the cyano group, S-alkylation of this thioamide gives a thioimidoester which is finally converted into the amidino or amidrazone compound, respectively, by treatment with ammonia or hydrazine or a salt thereof; or (b) for the synthesis of a compound of formula I, wherein $R^3$ means hydrogen or amino, comprises the conversion of a cyano compound of formula 10 by acidic alcoholysis into an acid addition salt of the corresponding imidoester, whose transformation using ammonia or hydrazine gives the amidino or amidrazone compound, respectively; or (c) for the synthesis of a compound of formula I, wherein $R^3$ means hydrogen, comprises the reduction of a compound of formula I, wherein $R^3$ means OH, or a corresponding alkanoyloxy compound; or (d) for the synthesis of a compound of formula I, wherein $R^3$ means OH or $NH_2$, comprises the conversion of a cyano compound of formula 10 using hydroxylamine or hydrazine into the corresponding hydroxyamidine or amidrazone compound, respectively; and (e) if desired, comprises the conversion of an obtained compound of formula I into an acid addition salt and/or conversion of an obtained acid addition salt into the corresponding compound of formula I or into another acid addition salt.

* * * * *